United States Patent [19]

Cope

[11] Patent Number: 5,330,972
[45] Date of Patent: Jul. 19, 1994

[54] METHOD OF IMPEDING APOPTOSIS OF CD4 CELLS IN PERSONS INFECTED WITH HUMAN IMMUNODEFICIENCY VIRUS

[75] Inventor: Frederick O. Cope, Worthington, Ohio

[73] Assignee: Abbott Laboratories, Abbott Park, Ill.

[21] Appl. No.: 69,264

[22] Filed: May 28, 1993

[51] Int. Cl.$^5$ .............................................. A61K 37/02
[52] U.S. Cl. ........................................ 514/2; 514/21; 530/378; 426/44; 426/46; 426/656; 426/800; 426/658; 426/419
[58] Field of Search ...................... 514/2, 21; 426/656, 426/46, 44, 800, 658, 419; 530/378

[56] References Cited

U.S. PATENT DOCUMENTS

| | | | |
|---|---|---|---|
| 4,100,024 | 7/1978 | Adler-Nissen | 195/29 |
| 4,850,704 | 7/1989 | Zimmerly et al. | 366/263 |
| 4,959,350 | 9/1990 | Frajaer et al. | 514/2 |

FOREIGN PATENT DOCUMENTS 246747 6/1989 European Pat. Off. .
91/13554 6/1991 PCT Int'l Appl. .

OTHER PUBLICATIONS

Monti et al. Am. J. Nutr vol. 55, pp. 1208 S-1214S (1992).
"The Role of Cell Renewal in the Ontogeny of the Intestine II Regulation of Cell Proliferation in Adult, Fetal and Neonatal Intestine", Klein et al., Journal of Pediatric Gastroenterology and Nutrition, vol. 2, pp. 204-228 (1983).
"Enteropathy Associated with the Acquired Immunodeficiency Syndrome", Kotler et al., Annals of Internal Medicine, vol. 101, No. 4, pp. 421-428 (1984).
"Reversible Malnutrition in AIDS", Weaver, Gastroenterology Clinics of North America, vol. 17, No. 3, pp. 545-561 (1988).
"Use of a Fiber-Containing Enteral Formulation in an AIDS Patient", Mandau et al., Nutrition Clinical Practice, vol. 4, No. 4, pp. 136-139 (1989).
"Less Diarrhea seen in HIV-Positive (HIV+) Patients on a Low-Fat, Elemental Diet", King et al., Proceedings of the V International Conference on AIDS, p. 466 (1989).
"Human Immunodeficiency Virus Infection and the Intestine", Griffin, Bailliere's Clinical Gastroenterology, vol. 4, No. 3, pp. 657-673 (1990).
Letter to Editor, Freed et al., American Journal of Gastroenterology, vol. 85, No. 4, p. 475 (1990).
"Malnutrition in Patients with AIDS", Hecker et al., Nutrition Reviews, vol. 48, No. 11, pp. 393-401 (1990).
The FASEB Journal, vol. 5, No. 10, pp. 2329-2330 (1991).
"Nutrition Support of HIV+ Patients", Dwyer, Henry Ford Hospital Medical Journal, vol. 39, No. 1, pp. 60-65 (1991).
"Nutritional Support of Patients with AIDS", Hickey, Surgical Clinics of North America, vol. 71, No. 3, pp. 645-664 (1991).

(List continued on next page.)

Primary Examiner—Howard E. Schain
Assistant Examiner—Choon Park Koh
Attorney, Agent, or Firm—Lonnie R. Drayer; Donald O. Nickey

[57] ABSTRACT

The apoptosis of CD4 cells in a person infected with the human immunodeficiency virus may be impeded by enterally feeding to the infected person a nutritional product which contains soy protein hydrolysate having a degree of hydrolysis in the range of about 14 to 17 and a molecular weight partition, as determined by size exclusion chromatography, wherein 30%-60% of the particles have a molecular weight in the range of 1500-5000 Daltons. The nutritional product also contains a source of intact protein. The nutritional product has a ratio, by weight, of n-6 to n-3 fatty acids of about 1.3:1 to 2.5:1. The nutritional product also contains a source of dietary fiber.

16 Claims, No Drawings

OTHER PUBLICATIONS

"Use of Nutrition Support in Patients with AIDS: A Four Year Retrospective Review", Brolin et al., Nutrition, vol. 7, No. 1, pp. 19–22 (1991).

"Dietary Manipulation of Methotrexate-Induced Enterocolitis", Shou et al., Journal of Parenteral and Enteral Nutrition, vol. 15, No. 3, pp. 307–312 (1991).

"Assesment of nutritional status, nutrient intake, and nutrition support in AIDS patients", Trujillo et al., Journal of the American Dietetic Association, vol. 92, No. 4, pp. 477–478 (1992).

"Nutritional Effects and Support in the Patient with Acquired Immunodeficiency Syndrome", Kotler, Journal of Nutrition, Mar. 1992 (3rd supplement), pp. 723–727 (1992).

"Apoptosis as a Mechanism of Cell Death in Peripheral Lymphocytes from HIV-1-Infected Individuals", Gougen, Immunodeficiency in HIV Infection and AIDS, pp. 115–126 (1992).

"The Programmed Cell Death Theory of AIDS Pathogenesis: Implications, Testable Predictions, and Confrontation with Experimental Findings", Amiesen, Immunodeficiency Reviews, vol. 3, pp. 237–246 (1992).

"Enteral Peptide Formulas Inhibit Radiation Induced Enteritis and Apoptosis in Intestinal Epithelial Cells and Suppress the Expression and Function of Alzheimer's and Cell Division Control Gene Products", Cope et al., The FASEB Journal, Mar. 15, 1991, p. A931.

"Induction of Expression of the Alzheimer's Gene by Radiation in Intestinal Epithelial Cells; Implications for a Novel Paradigm in Gene-Directed Cell Death (Apoptosis)", Tomei et al., The FASEB Journal, Mar. 19, 1991, p. A1606.

"Inhibition of the Intestinal Expression of the Alzheimer's and Cell Division Control Gene Product and Functions by Enteral Peptides Marks the Inhibition of Radiotherapy Induced Enteritis and Apoptosis", Cope et al., Abstract #48, Proceedings of 82nd Annual Meeting of American Assoc. for Cancer Research (1991).

"Prophylactic Enterotrophic Peptide Inhibition of Radiotherapy Induced Enteritis is Marked by Down Regulation of the Expression of the Amyloid Beta protein, CK-II and Apoptosis", Cope et al., Abstract No. 1537, Proceedings of the 83rd Annual Meeting of the American Association for Cancer Research (1992).

METHOD OF IMPEDING APOPTOSIS OF CD4 CELLS IN PERSONS INFECTED WITH HUMAN IMMUNODEFICIENCY VIRUS

FIELD OF THE INVENTION

The present invention relates generally to a method of impeding the apoptosis of CD4 cells in a person infected with human immunodeficiency virus (HIV) by enterally feeding to an HIV infected person a nutritional product which has been formulated to address the nutritional needs of persons infected with HIV.

BACKGROUND OF THE INVENTION

A profound wasting disease in humans associated with *Pneumocystis carinii* pneumonia was first described in the United States in 1981. The investigation of the symptoms associated with this disease ultimately focused public health and political structures on a disease described as acquired immunodeficiency syndrome (AIDS). AIDS is defined by infection with the human immunodeficiency virus (HIV), and by the onset of several opportunistic infections, syndromes, and/or malignancies. These include, but are not limited to, tuberculosis, *Pneumocystis carinii* pneumonia, *Salmonella bacteremia*, Kaposi's sarcoma, *Mycobacterium avium* intracellulare, herpes simplex, toxoplasmosis, cytomegalovirus (CMV), dementia complex, and wasting syndrome.

The cell types infected by HIV play a role in defining the efforts of the virus on patterns of infection, and ultimately the effect of the disease on the metabolic and nutritional state of a person infected with HIV. The immune system develops several types of cells to deal with infection, including B and T lymphocytes, which produce antibodies and directly attack the invading pathogen. These cells and others, including macrophages, monocytes, and other cell types involved in the immune response, communicate through protein factors which they secrete (cytokines) and/or through the types of proteins and glycoproteins they display on their surface.

Health care professionals dealing with HIV-positive and AIDS patients face a multitude of management issues, including control of opportunistic infections and malignancies. Two major factors underlying how a patient may respond to the therapies required to manage the disease are: (a) the nutritional status of the patient early in the infectious process, and (b) the ability of the patient to take in and tolerate adequate nutrition.

There is disclosed herein a liquid nutritional product for enteral feeding which is formulated, on the basis of the latest and most compelling research, to meet the specific nutrient needs of persons infected with HIV. This calorie and nutrient-dense, low fat nutritional product contains enterotrophic peptides, a fat source high in omega-3 fatty acids, and fiber. Enterotrophic peptides appear to modulate a particular receptor pathway in cells which reduces the expression of apoptotic genes and alters the phosphorylation of cell division control protein. The peptides significantly reduce the expression of the apoptotic-associated gene, amyloid beta precursor protein, and apoptotic rescue protein. (This protein is a marker for the induction of cell death). This nutritional regimen results in a reduction in the rate of intestinal cell death. These formula components promote changes in the gastrointestinal tract that result in improved nutritional and physiological status for a HIV-infected person. The vitamin and mineral profile of this nutritional product provides for repletion of the nutrients for which HIV-positive persons have been shown to be at risk of depletion or deficiency. The nutritional product also contains $\beta$-carotene.

The nutritional product of the present invention is acceptable total enteral support and may be consumed, either orally or by tube feeding. Flavor variety Orange Cream and Chocolate flavors are disclosed herein, promotes compliance when the nutritional product is used as an oral supplement or as a total oral diet when a person's condition precludes intake of solid foods.

DISCUSSION OF PRIOR ART

There has been a great deal written about nutritional support of persons infected with HIV.

Villous atrophy of the small intestine may be detected early in the course of HIV infection and in the absence of enteropathogens, so it has been postulated that the intestinal tract may be severely affected by HIV. The histological appearance of villous atrophy seen in HIV infection is unlike the classic villous atrophy seen in gluten-sensitive enteropathy or tropical sprue because the enterocytes appear normal and there is no increase in intraepithelial lymphocytes. This resembles the villous atrophy seen in graft versus host disease of bone marrow transplantation, and this raises the possibility that an immune response within the mucosa may be responsible. Griffin, "Human Immunodeficiency Virus Infection and the Intestine", BAILLIERE'S CLINICAL GASTROENTEROLOGY", Vol. 4, No. 3, pages 657–673 (1990). Apoptosis of crypt cells in AIDS patients was reported soon after the disease was identified. Kotler et al., "Enteropathy Associated with the Acquired Immunodeficiency Syndrome", ANNALS OF INTERNAL MEDICINE, Vol 101, No. 4 pages 421–428 (1984).

Trujillo et al, "Assessment of nutritional status, nutrient intake, and nutrition support in AIDS patients", JOURNAL OF THE AMERICAN DIETETIC ASSOCIATION, Vol.92, No.4, pages 477–478 (1992) reports observations that hospitalized AIDS patients can consume only 10% of estimated basal energy needs and 65% of protein needs, which does not account for the increased needs of hypermetabolism associated with acute infection or any physical activity. Patients with AIDS have moderate to severe metabolic stress similar to that found in other critically ill patients. This stress, coupled with the anorexia and malabsorption associated with the disease, promotes malnutrition. Irrespective of any possible specific relationship between nutrition and the HIV disease process, malnourished patients will be debilitated and unable to function optimally. Malnutrition in general affects five areas of functionality: reproductive competence, immunocompetence, work performance and/or behavioral performance and cognition. THE FASEB JOURNAL, Vol. 5, No. 10, pages 2329–2330, at page 2330 (1991)

Food-borne infections must be scrupulously avoided in immunosupressed patients, because what would be a minor incident for a healthy person might become life threatening. HIV infected patients are 300 times more susceptible to salmonella than healthy persons if they ingest contaminated food. Dwyer, "Nutrition Support of HIV+ Patients", HENRY FORD HOSPITAL MEDICAL JOURNAL, Vol. 39, No. 1, pp. 60–65, at page 62 (1991). Kotler, "Nutritional Effects and Support in the Patient with Acquired Immunodeficiency Syndrome", JOURNAL OF NUTRITION, March, 1992 (3rd supplement), pages 723-727 describes some micronutrient deficiencies in AIDS patients: (a) low serum zinc and selenium; (b) vitamin B-12 malabsorption and subnormal serum vitamin B-12 concentrations; (d) the prevalence of folate deficiency which varies depending upon the dietary habits of the affected population; and (d) malabsorption of fat-soluble micronutrients, such as vitamin E, β-carotene and essential fatty acids.

In a letter to the editor in the AMERICAN JOURNAL OF GASTROENTEROLOGY, Vol. 85, Issue 4, P. 475 (1990), Freed et al champions the use of enteral nutritional support for AIDS and cancer patients, as opposed to parenteral feeding, whenever possible.

The administration of specific nutrients or diets including essential fatty acids, Cobalamin, and zinc has been attempted in patients with AIDS-related complex (ARC) or AIDS because biochemical indicators of these nutrients are altered for the worse in symptomatic HIV infected patients. However, little symptomatic improvement or amelioration in immune status was demonstrated. Dwyer, "Nutrition Support of HIV+ Patients", HENRY FORD HOSPITAL MEDICAL JOURNAL, Vol. 39, No. 1, pp. 60-65, at page 60 (1991).

Mandau et al., "USE OF A FIBER-CONTAINING ENTERAL FORMULATION IN AN AIDS PATIENT", Nutrition Clinical Practice, Vol. 4, Issue 4, pp. 136-139 (1989) describe an AIDS patient who was fed a variety of nutritional supplements, but continued to suffer from bad diarrhea until fed a high residue nutritional product. However, King et al, "LESS DIARRHEA SEEN IN HIV-POSITIVE (HIV+) PATIENTS ON A LOW-FAT, ELEMENTAL DIET", PROCEEDINGS OF THE V INTERNATIONAL CONFERENCE ON AIDS, page 466 (1989) suggests that dietary management with a low-fat, low-residue, elemental diet may be a useful adjunctive therapy to help maintain body weight and reduce diarrhea in some HIV infected patients.

The desirability of a diet for AIDS patients which is low in fat but high in fiber is suggested by Weaver in "Reversible Malnutrition In AIDS", GASTROENTEROLOGY CLINICS OF NORTH AMERICA, Vol. 17, No. 3, pp. 545-561 (1988). Weaver teaches that Vivonex® TEN (manufactured by Norwich Eaton Chemicals, Inc., Norwich, N.Y.), has proved to be an excellent supplement or diet for AIDS patients with normal or compromised gut function. Vivonex® is packaged in powdered form and is mixed with water or a liquid of choice (to modify the bitter taste of the amino acids) for oral consumption or tube feeding. This publication also presents other several suggested regimens for nutritional support for AIDS patients, but concludes, at page 559 that "there is no single nutritional therapy regimen that can be utilized in the treatment of all of these patients. Therefore, we recommend special individualized oral diets combined with food supplements and enteral and parenteral diets in the treatment of ARC/AIDS patients."

Hickey, "Nutritional Support of Patients with AIDS", SURGICAL CLINICS OF NORTH AMERICA, Vol. 71, No. 3, pages 645-664 (1991) presents a good review of the state of nutritional support for AIDS patients. He states that the primary goal of nutritional therapy for these patients is to maintain metabolic homeostasis (normal functional indices, positive nitrogen balance, and a stable weight). He advocates feeding an elemental nutritional product, which contains protein in the form of free amino acids, either as a supplement or sole source of nutrition, because the free amino acids having molecular weights of less than 500 are absorbed rapidly in the presence of compromised gut function. However, he also indicates that not all AIDS patients are able to tolerate an elemental nutritional product. Hecker et al, "Malnutrition in Patients with AIDS", NUTRITION REVIEWS Vol 48, No 11 pages 393-401 at page 397 (1990) suggests that the consumption of a low-fat, low residue elemental diet may be beneficial for some AIDS patients.

The recommendations to feed a free amino acid elemental diet to AIDS patients are not without controversy. For instance, Brolin et al., "Use of Nutrition Support in Patients with AIDS: A Four-Year Retrospective Review", NUTRITION, Vol. 7, No. 1, pages 19-22, at page 21 (1991) notes that authors such as Hickey and Weaver did not describe the results of their use of elemental diets in AIDS patients with diarrhea. In Brolin et al's experience such patients will not drink sufficient quantities of any enteral diet and do not tolerate enteral tube feedings because of exacerbated gut dysfunction, such that in their experience parenteral nutritional support has been the only useful option in AIDS patients with diarrhea.

There are some compelling arguments against feeding an elemental diet to an AIDS patient. While not specifically directed to AIDS patients, Klein et al, "The Role of Cell Renewal in the Ontogeny of the Intestine. II. Regulation of Cell Proliferation in Adult, Fetal and Neonatal Intestine", JOURNAL OF PEDIATRIC GASTROENTEROLOGY AND NUTRITION, Vol. 2, pages 204-228, at page 211 (1983) relates that (a) an elemental diet (VIVONEX®) has been shown to decrease cell renewal and villus size in both the jejunum and ileum; (b) the addition of bulk to the elemental diet does increase cell renewal, but does not alter villus height; and (c) gastrin levels are drastically lowered in elemental diet-fed rats, but it is possible that there is more direct effect of dietary consistency on the mucosa.

While not specifically directed to AIDS patients, the effects of diet upon chemotherapy induced enterocolitis are reported in "Shou et al., "Dietary Manipulation of Methotrexate-Induced Enterocolitis", JOURNAL OF PARENTERAL AND ENTERAL NUTRITION, Vol. 15, No. 3, pages 307-312 (1991). The results of this study suggested that patients unable to ingest a regular diet while undergoing chemotherapy may benefit from a diet with polypeptides as a nitrogen source rather than an elemental diet. This publication advocates that elemental liquid diets cause changes in intestinal microflora characterized by a significantly increased level of Gram-negative bacteria. it is alleged that translocation of bacteria from the intestinal tract through the epithelial mucosa to cause infections may result at least in part from bacterial overgrowth and that administration of a liquid nutritional diet results in atrophy of the intestinal mucosa with reduced mucosa villous height and crypt depth and other undesirable results.

DETAILED DESCRIPTION OF THE INVENTION

A nutritional product according to the present invention is a high protein, low fat, calorically dense product for HIV infected and AIDS patients. The nutritional product of the present invention meets the unique nutrient requirements of this population. An objective of the present invention is to maintain the gut architecture of the HIV infected person in a state which is at least equal to normal gut architecture relative to a disease state. Other objectives of the present invention are a reduction in the potential for dehydration, and a reduction in the amount of medication needed for treating diarrhea, which reduces the likelihood of interaction between anti-diarrhea medications and other medications that the HIV infected person may be using. The maintenance of gut architecture lessens or eliminates an inflammatory response in the form of enteritis. Histological and endoscopic evaluations of HIV infected persons who had been fed the nutritional product of the present invention indicated that the above described benefits had been manifested. Yet another objective of the present invention is to impede the deterioration of the immune system of an HIV infected person.

The nutrient base for the enteral liquid nutritional product of the present invention is 1515 calories per day which are provided in five 8 fluid ounce servings. However, it is understood that the enteral liquid nutritional product may be consumed either as a sole source of nutrition or as a nutritional supplement, as recommended by an attending physician. Put another way, an 8 fluid ounce serving of the new nutritional product provides about 303 calories and a liter provides about 1,280 calories. The caloric density of the new nutritional product is in the range of about 1.2 to 1.35 cal/ml, most preferably about 1.28 cal/ml. This high caloric density allows the patient to consume more calories in a smaller volume of product, which is extremely important in instances of impaired appetite. The nutritional profile of the new enteral nutritional product is presented in TABLE 1.

TABLE 1
NUTRITIONAL PROFILE OF PRODUCT

| NUTRIENT | TARGET PER LITER | TARGET RANGE PER LITER | TARGET PER 8 FLUID OUNCE |
|---|---|---|---|
| Fat, g | 22.8 | 22.8–24.8 | 5.4 |
| Protein, g | 60.0 | 60.0–62.7 | 14.2 |
| Carbohydrate, g | 215.8 | 200–225 | 49.0 |
| Vitamin A, IU | 4223 | 4223–7580 | 1000 |
| β-carotene, mcg | 5068 | 5068–7000 | 1200 |
| Vitamin E, IU | 38.1 | 38.1–53 | 9 |
| Vitamin D, IU | 338 | 338–485 | 80 |
| Vitamin K, mcg | 67.6 | 67.6–160 | 16 |
| Calcium, mg | 845 | 845–1268 | 200 |
| Magnesium, mg | 338 | 338–507 | 80 |
| Sodium, mg | 1014 | 913–1115 | 235 |
| Potassium, mg | 2619 | 2357–2881 | 635 |
| Phosphorus, mg | 845 | 845–1268 | 200 |
| Chloride, mg | 1479 | 1331–1627 | 345 |
| Iodine, mcg | 127 | 127–191 | 30 |
| Zinc, mg | 15.9 | 15.9–23.7 | 3.75 |
| Copper, mg | 2.54 | 254–3.8 | 0.6 |
| Manganese, mg | 5.28 | 5.28–7.9 | 1.25 |
| Iron, mg | 19.1 | 19.1–28.5 | 4.5 |
| Selenium, mcg | 60 | 60–203 | 14 |
| Chromium, mcg | 85 | 85–203 | 20 |
| Molybdenum, mg | 127 | 127–253 | 30 |
| Pyridoxine ($B_6$), mg | 3.38 | 3.38–5.3 | 0.8 |
| Niacin, mg | 25.4 | 25.4–49 | 6 |
| Pantothenate, mg | 12.7 | 12.7–29 | 3 |
| Folic Acid, mcg | 507 | 507–1075 | 120 |
| Thiamine ($B_1$), mg | 3.17 | 3.17–8.0 | 0.75 |
| Riboflavin ($B_2$), mg | 2.88 | 2.88–6.2 | 0.68 |

TABLE 1-continued
NUTRITIONAL PROFILE OF PRODUCT

| NUTRIENT | TARGET PER LITER | TARGET RANGE PER LITER | TARGET PER 8 FLUID OUNCE |
|---|---|---|---|
| Cyanocobalamin ($B_{12}$), mcg | 50.68 | 50.68–97 | 12 |
| Biotin, mcg | 381 | 381–950 | 90 |
| Vitamin C, mg | 381 | 381–825 | 90 |
| Choline, mg | 212 | 212–750 | 50 |
| Taurine, mg | 212 | 212–320.4 | 50 |
| Carnitine, mg | 127 | 127–299.4 | 30 |
| Fiber, g | 8.9 | 8.9–11.6 | 2.1 |

Body protein stores are in a constant state of breakdown (catabolism) and synthesis (anabolism), a process known as protein turnover. Persons with HIV infection experience metabolic "ebbs" and "flows" from the effect of ongoing and intercurrent infection. During active phases of infection, when patients are hypermetabolic, catabolic processes dominate. During quiescent phases between active and intercurrent infection, anabolism predominates. Providing appropriate levels of energy, protein and other nutrients enhances nitrogen and tissue synthesis during anabolism. It has been reported that enteral nutrition support can replete body-cell mass in malnourished AIDS patients.

The protein system in a preferred embodiment of the nutritional product of the present invention comprises by weight: about 78% soy protein hydrolysate and about 22% sodium caseinate.

The soy protein hydrolysate which is used as a source of protein in the nutritional product of the present invention may be manufactured using a process taught in U.S. Pat. No. 4,100,024, which is incorporated herein for the purpose of teaching a process for manufacturing a soy protein hydrolysate for use in the nutritional product of the present invention. Briefly, this is a process for the preparation of polypeptides from soy protein soluble in aqueous media at pH's in the range of 2 to 7 which involves: hydrolyzing soy protein with a microbial, alkaline proteinase in a concentration ranging from 4 to 25 Artson units per kg of soy protein at a substrate concentration of between 5 and 20% w/w soy protein, at a pH in the range of from 7.5 to 8.5, until a degree of hydrolysis in the range of from about 8 to 15% is attained, whereafter the enzyme is inactivated by reduction of the pH with a food grade acid, then recovering the supernatant from the precipitate. However, it is understood that a soy protein hydrolysate produced by any other process which has the characteristics elaborated upon herein may be used in the practice of the present invention.

An example of a nutritional product containing such a soy protein hydrolysate is taught in U.S. Pat. No. 4,959,350, but this prior art nutritional product has a pH of lower than 4.5 (as compared to a pH of 6.4 to 6.6 in the product of the present invention) and has an osmolality of below about 350 mosm/kg water (as compared to about 660 mosm/kg water in the nutritional product of the present invention). This prior art nutritional product may be further distinguished from the nutritional product of the present invention by the fat composition, fiber content, and the vitamin and mineral profiles of the product of the present invention.

The nutritional product of the present invention has been manufactured using soy protein hydrolysate obtained from NOVO Industri A/S, Bagsvaerd, Denmark, who manufactured the soy protein hydrolysate according to the above described process. The properties of a soy protein hydrolysate which is suitable for use in the practice of the present invention have been determined by actual analysis of samples from several lots of soy protein hydrolysate obtained from NOVO Industri and/or specifications selected in accordance with desired properties.

It is believed to be very important that the soy protein hydrolysate used in the practice of the invention comprise, by weight, not less than 76%, preferably not less than 80% protein, not more than 1% fat, and not more than 5.5%, preferably not more than 4.8% ash. It is also believed to be very important that a 5% slurry (by weight) of the soy protein hydrolysate in water has a pH in the range of about 4.2 to 4.3, but in any instance less than 4.5. It is believed to be important that the degree of hydrolysis of the soy protein hydrolysate (AN/TN×100) be in the range of about 14 to 17 and most preferably about 16.

The amino acid profile of the soy protein hydrolysate that has been used in the practice of the present invention is presented in Table 2, and the mineral profile is presented in Table 3. The molecular weight profile is presented in Table 4 for soy protein hydrolysate (SPH) having about a 16% degree of hydrolysis with the approximate molecular weight partition determined by size exclusion chromatography of samples from 4 lots of SPH. The molecular weight profile of the soy protein hydrolysate is believed to be very important because particles sizes are related to the physical stability and biological functionality of an enteral nutritional product which contains the SPH. That is to say, for the SPH used in the nutritional product of the present invention the molecular weight profile indicates a large peptide content (consisting of particles having a molecular weight of 1500–5000 Daltons) and a small free amino acid content. About 30%–60%, by weight, of the SPH comprises particles having molecular weights of 1500–5000 Daltons. The free amino acid content is less than 1%, by weight of the soy protein hydrolysate, or put another way less than 1 g/100 g of the soy protein hydrolysate. Preferably, the enteral nutritional product of the invention contains no other source of free amino acids. However, it is within the scope of the invention for the nutritional product to contain up to about 13 g/100 g of protein as free amino acids. The low free amino acid content is an advantage for osmolality and flavor characteristics of an enteral nutritional product. The mineral profile of the soy protein hydrolysate is believed to be very important because it supplies most of the trace and ultratrace minerals in the nutritional product.

TABLE 2

AMINO ACID PROFILE OF SOY PROTEIN HYDROLYSATE (g/100 g)

| Aspartic acid | 9.8–10.4 |
| Threonine | 2.9–3.2 |
| Serine | 3.7–4.4 |
| Glutamic Acid | 17.0–18.1 |
| Proline | 4.4–4.9 |
| Glycine | 3.2–3.3 |
| Alanine | 3.0–3.2 |
| Valine | 2.9–3.6 |
| Methionine | 0.9–1.1 |
| Isoleucine | 3.0–3.7 |
| Leucine | 5.1–5.3 |
| Tyrosine | 2.7–2.9 |
| Phenylalanine | 3.3–3.5 |

TABLE 2-continued

AMINO ACID PROFILE OF SOY PROTEIN HYDROLYSATE (g/100 g)

| Histidine | 2.0–2.2 |
| Lysine | 5.5–5.8 |
| Arginine | 6.3–6.7 |
| Tryptophan | 0.3–0.7 |
| Cystine | 1.3–1.4 |
| Free Amino Acids | 0.4–0.7 |

TABLE 3

MINERAL PROFILE OF SOY PROTEIN HYDROLYSATE

| | Preferred Range | Most Preferred Range |
| --- | --- | --- |
| Calcium, mg/100 g | 170–350 | 170–260 |
| Sodium, mg/100 g | 370–650 | 370–520 |
| Potassium, mg/100 g | 180–600 | 180–470 |
| Magnesium, mg/100 g | 270–550 | 270–400 |
| Phosphorus, mg/100 g | 900–1500 | 900–1200 |
| Chloride, mg/100 g | 1400–2500 | 1400–2250 |
| Iron, mg/100 g | 13–25 | 13–20 |
| Zinc, mg/100 g | 3–6 | 3–6 |
| Manganese, mg/100 g | 4–8 | 5–7 |
| Copper, mg/100 g | 0.5–1.5 | 0.5–1.0 |
| Vanadium, ppm | trace–15 | 8–12 |
| Selenium, ppb | trace–350 | 150–300 |
| Chromium, ppm | trace–2.9 | 1.5–2.3 |
| Molybdenum, ppm | trace–3.7 | 2–3 |

TABLE 4

MOLECULAR WEIGHT PARTITION FOR SPH (AS DETERMINED BY SIZE EXCLUSION CHROMATOGRAPHY OF SAMPLES FROM FOUR DIFFERENT LOTS OF SPH)

| Molecular Wt. (in Daltons) | % of Particles With This Molecular Wt. | | |
| --- | --- | --- | --- |
| | Average | Std. Deviation | Range |
| >5000 | 3.3 | 1.96 | 1.70–5.96 |
| 2000–5000 | 25.8 | 5.42 | 19.50–30.75 |
| 1500–2000 | 20.5 | 7.41 | 13.10–27.50 |
| 1200–1500 | 12.5 | 0.92 | 11.80–13.80 |
| 1000–1200 | 8.2 | 0.83 | 7.30–9.00 |
| 500–1000 | 19.5 | 3.02 | 16.80–23.80 |
| <500 | 10.2 | 6.03 | 5.30–19.00 |

Preferably, the soy protein hydrolysate used in the practice of the present invention has a molecular weight profile as determined by size exclusion chromatography wherein 30%–60% of the particles have a molecular weight in the range of 1500–5000 Daltons. The use of soy protein hydrolysate having other molecular weight profiles did not result in acceptable products.

It was discovered that the soy protein hydrolysate used in the nutritional product of the present invention does not yield a shelf stable product in the absence of intact protein. Once a protein is hydrolyzed, it looses its primary and secondary structure and consequently some of its functionality, including emulsifying properties. Therefore, it does not have surfactant properties and is unable to stabilize the formulation resulting in phase separation. Various approaches were investigated to attempt to stabilize a liquid product containing this particular soy protein hydrolysate.

Three different emulsifiers, and combinations thereof, were evaluated, but the most effective emulsifier is Panodan ® which is distributed by Grinstead of Danisco, Denmark. Panodan ® is diacetyl tartaric acid esters of mono-diglycerides and is an anionic surfactant with a very hydrophilic component attached. Panodan ® is generally regarded as safe (GRAS) for use in nutritional products for human consumption. Panodan ® works by imparting a negative charge to the fat globules in the nutritional product, thus, causing them to electrostatically repel each other so that no flocculation or coalescence occurs. The soy protein hydrolysate could stay in an emulsion for about two weeks with Panodan ®, but no other protein source present. It is, however, believed that sodium stearoyl lactylate could also be used as an emulsifier, but this emulsifier has not yet been classified as GRAS by the U.S. Food and Drug Administration.

The use of starches to stabilize an emulsion containing the soy protein hydrolysate was investigated, but this approach was abandoned because the viscosity of the emulsion was too high.

The use of intact proteins as a stabilizer was also investigated. The stabilizing power of proteins has long been recognized. Caseinates, for example, have a high electrical charge that make them hydrophilic and have several hydrophobic groups. This, and their random coiled molecular structure, makes them ideal emulsifiers with a strong preference for fat/water interfaces. It was discovered that a protein system comprising, by weight, at least 10%-30% sodium caseinate with the remainder being the soy protein hydrolysate described herein, in combination with Panodan ® yielded an emulsion having satisfactory stability with regards to phase separation.

The protein system in a preferred embodiment of the new enteral nutritional product comprises, by weight, about 78% soy protein hydrolysate and about 22% sodium caseinate.

It is to be understood that the component(s) of the protein system of a nutritional product of the present invention comprising intact protein could comprise any suitable source of intact protein, such as pea protein and whey protein concentrate, whether in place of or in addition to the sodium caseinate. For example, if it were desired to reduce the pH of the nutritional product to a more acidic level, at which sodium caseinate is not stable, then a source of intact protein such as a whey protein concentrate or isolate could be substituted for the sodium caseinate in an appropriate quantity.

A typical Amino Acid profile (mean of five batches of the nutritional product of the present invention) is presented in TABLE 5.

TABLE 5

| AMINO ACID PROFILE OF NUTRITIONAL PRODUCT | | | |
|---|---|---|---|
| Amino Acid | mg/g Protein | mg/ Liter | Range |
| Histidine | 26.1 | 1566.0 | 25.2–26.5 |
| Isoleucine | 38.7 | 2322.0 | 36.8–41.1 |
| Leucine | 70.8 | 4248.0 | 68.9–72.3 |
| Lysine | 68.6 | 4116.0 | 67.3–69.7 |
| Methionine | 14.8 | 888.0 | 13.6–16.3 |
| Phenylalanine | 42.8 | 2568.0 | 42.1–43.8 |
| Threonine | 39.7 | 2382.0 | 38.4–40.6 |
| Iryptophan | 6.5 | 390.0 | 6.0–7.1 |
| Valine | 40.9 | 2454.0 | 38.4–43.5 |
| Phe + Tyr | 78.2 | 4692.0 | 76.9–79.4 |
| Met + Cystine | 28.9 | 1734.0 | 27.2–30.2 |
| Alanine | 36.9 | 2214.0 | 36.1–37.7 |
| Arginine | 68.6 | 4116.0 | 67.1–70.1 |
| Aspartic Ac. | 115.1 | 6906.0 | 111.2–118.0 |
| Cystine | 14.1 | 846.0 | 13.0–14.5 |
| Glutamic Ac. | 216.7 | 13002.0 | 207.3–221.0 |
| Glycine | 36.0 | 2160.0 | 35.0–37.0 |
| Proline | 70.5 | 4230.0 | 66.8–72.3 |
| Serine | 54.2 | 3252.0 | 52.8–56.1 |

TABLE 5-continued

| AMINO ACID PROFILE OF NUTRITIONAL PRODUCT | | | |
|---|---|---|---|
| Amino Acid | mg/g Protein | mg/ Liter | Range |
| Tyrosine | 35.4 | 2124.0 | 34.7–35.8 |

One of the problems encountered by persons infected with HIV is diarrhea. The nutritional product of the present invention provides nutritional support to combat HIV inflicted diarrhea. Dietary fiber, in the form of soy polysaccharides, adds bulk to the stool and helps to increase water retention. As used herein and in the claims "dietary fiber", or "fiber" is understood to refer to plant material that is undigested by human enzymes. Fiber may be partially digested by bacteria in the ileocecal region and in the colon, resulting in the production of short-chain fatty acids (acetate, propionate and butyrate) and gases (methane and carbon dioxide). Fiber is known to be beneficial in regulating bowel function in diarrhea. Soy polysaccharide, the source of dietary fiber in the nutritional product of the present invention has been shown to produce short-chain fatty acids in the intestine. The nutritional product of the present invention contains about 8.9–11.6 g/L, preferably about 8.9 g/1 (2.1 g/8 fluid ounces) of dietary fiber from soy polysaccharide.

The fat system is the nutritional product of the present invention consists, by weight, of about 70% canola oil; about 20% medium chain triglycerides (MCT) oil (e.g. fractionated coconut oil); and about 10% fish oil. The emulsifiers used in the nutritional product of the present invention are diacetyl tartaric acid esters of mono-diglycerides. They constitute about 5% of the oil blend. The fatty acid profile of the nutritional product is presented in TABLE 6.

TABLE 6

| FATTY ACID PROFILE OF NUTRITIONAL PRODUCT | |
|---|---|
| FATTY ACID | % OF TOTAL FATTY ACIDS BY WEIGHT |
| Caprylic (8:0) | 10–14.5 |
| Capric (10:0) | 5–8.5 |
| Lauric (12:0) | about 0.08 |
| Myristic (14:0) | 0.58–0.70 |
| Palmitic (16:0) | 4.3–5.7 |
| Palmitoleic (16:1n-7) | 0.9–1.1 |
| Stearic (18:0) | 3.5–5.0 |
| Oleic (18:1n-9) | 41.0–42.0 |
| Linoleic (18:2n-6) | 13.8–17.1 |
| Alpha-Linolenic (18:3n-3) | 5.6–6.4 |
| Stearidonic (18:4n-3) | about 0.3 |
| Eicosanoic (20:1n-9) | 1.1–1.2 |
| Eicosapentaenoic (20:5n-3) (EPA) | 2.4–3.4 |
| Behenic (22:0) | 0.2–0.4 |
| Erucic (22:5n-3) | 0.3–0.4 |
| Docosapentaenoic (22:1n-9) | about 0.2 |
| Docosahexaenoic (22:6n-3) (DHA) | 1.3–1.4 |
| Nervonic (24:1n-9) | 0.0–0.1 |
| Others | 0.4–1.1 |
| Polyunsaturated Fatty Acids | about 26% |
| Saturated Fatty Acids | about 29% |
| Ratio of Polyunsaturated to Saturated | about 0.9% |
| Ratio of total n-6 to total n-3 fatty acids | 1.3:1–2.5:1 |

The refined deodorized fish oil used in the nutritional product of the present invention contains about 45% total n-3 polyunsaturated fatty acids, of which about 28% are Eicosapentanoic acid (EPA, C20:5n-3) and 13% are Docosahexanoic acid (DHA, C22:6n-3). These unsaturated fatty acids make the oil very prone to oxidation. Thus, approximately 7000 ppm of natural mixed tocopherols are added to the oil by the supplier before shipment to prevent oxidation. Upon arrival the oil is kept under nitrogen and refrigeration until it is used. The shelf-life assigned to this commodity is only 10 days to assure that the oil is of optimal quality at the time of use. The nutritional product has been manufactured using a fish oil manufactured from sardines and has been obtained from Mochida International in Shijuku-Ku, Tokyo, Japan.

Although there is no specific dietary requirement for total fat, some is needed to provide essential fatty acids, to carry fat-soluble vitamins, and to facilitate their absorption. N-3 fatty acids, for example from fish oil, reduce prostaglandin production and the expression of certain oncogenes, e.g..RAS. N-3 fatty acids also reduce the expression of apoptotic genes (cell death genes). The liquid nutritional product of the present invention contains not less than 1900 mg of n-3 fatty acids per liter (450 mg per 8 fluid ounces). The ratio, by weight, of the sum of the n-6 fatty acids to the sum of the n-3 fatty acids in the nutritional product is about 1.3:1 to 2:5 to 1, preferably about 1.5: 1.

The fatty acid profile of the nutritional product of the present invention meets the recommendation of the American Heart Association for less than 10% of calories from saturated fat and not more than 10% of calories from polyunsaturated fat.

The carbohydrate system in the nutritional product of the present invention consists of a mixture of complex carbohydrates and simple sugars which are provided by the following product ingredients in the following proportions, by weight: about 72.1% hydrolyzed cornstarch; about 22.8% sucrose; and about 5.1% soy polysaccharide.

The stabilizer used in the nutritional product of the present invention is a mixture of Kappa and Iota carrageenan at 350 ppm level. Carrageenan is a high molecular weight linear polysaccharide obtained from red seaweed plants.

The nutritional product of the present invention provides at least 100% of the US RDA for vitamins and minerals in 1184 ml (five 8 fluid ounce servings). The oil soluble vitamins (Alpha-tocopheryl acetate, vitamin A palmitate, Phylloquinone, Vitamin D3) are added as a premix. The water soluble vitamins (Niacinamide, d-calcium pantothenate, Thiamine hydrochloride, Pyridoxine hydrochloride, Riboflavin, Folic acid, Biotin, Cyanocobalamin) are also added as a premix. Beta Carotene is added as a 30% solution in vegetable oil. Choline chloride, Taurine, L-Carnitine, Ascorbic acid and additional Cyanocobalamin are added individually.

The soy protein hydrolysate in the formulation provides 100% of the chromium and molybdenum needed. The remaining minerals come from sodium citrate, calcium carbonate, ultramicronized tricalcium phosphate (TCP), magnesium phosphate dibasic, copper sulfate, sodium selenate, zinc sulfate, manganous sulfate, ferrous sulfate and potassium iodide. It has been observed that additional TCP may need to be used if the level of phytate in the soy protein hydrolysate is so high that it renders too much of the phosphorus from the SPH biologically unavailable.

The concentrated levels of vitamins and minerals, which are presented in TABLE 1, enable the nutritional product of the present invention to meet the nutritional requirements of enterally fed patients with a smaller volume of the product. HIV infected patients often need volume restriction because of gastrointestinal tract problems, or drug-or treatment-related anorexia, nausea, and/or vomiting.

The nutritional product of the present invention contains $\beta$-carotene, a carotenoid compound that has provitamin A activity. However, unlike vitamin A, $\beta$-carotene is not associated with toxicity and, therefore, may be used as a source of retinol equivalents in the diet without introducing toxicity concerns. Vitamin A has been shown to reverse some of the immunosuppression associated with thermal injury and radiation injury.

The levels of vitamins E and C, folic acid, and vitamin $B_{12}$ provided by 1184 mL (five 8 fluid ounce servings) per day of the nutritional product of the present invention greatly exceed the US RDA's for these nutrients in order to encourage adequate storage in the early phases of the disease and to attempt to counteract the deficiencies in these vitamins observed in the later stages. The minerals iron, magnesium, zinc and selenium have been included at levels intended to counteract depletion or deficiencies of these nutrients which have been observed as the disease progresses.

Another problem encountered by persons infected with HIV is cachexia (weight loss). N-3 fatty acids provided, for example, by fish oil and canola oil, significantly stay cachexia by inhibiting cachectins and tumor necrosis factor, which are involved in metabolic changes. The cachectins reduce an individual's ability to maintain lean body mass in the face of increased lipogenesis (exchanging lean muscle for fat). The high caloric density of the nutritional product of the present invention, as well as the enterotrophic peptides from the soy protein hydrolysate, provides a source of high nitrogen to maintain protein synthesis. The nutritional product of the present invention has a very low calorie: nitrogen ratio of about 135:1. The above indicated benefits have been indicated in HIV infected persons fed the nutritional product of the present invention by evaluating body composition (% lean body mass and body fat), intermediary metabolism using stable isotopes, and measuring cytocines.

Another problem encountered by persons infected with HIV is the depletion of specific nutrients, such as selenium, magnesium, zinc, vitamin $B_6$, vitamin $B_{12}$, folate, and beta carotene. As indicated in TABLE 1, the nutritional product of the present invention provides these nutrients in amounts which far exceed the U.S. RDA for these nutrients.

Another problem encountered by persons infected with HIV is an increased risk of cardiomyopathy. The nutritional product of the present invention contains nutrients which reduce the risk of cardiomyopathy. These ingredients include selenium, fish oil, $\beta$-carotene and vitamin E.

Appropriate amounts of electrolytes (sodium, potassium and chlorides) are required for the maintenance of fluid status and other important functions such as the synthesis of protein. Potassium, in particular, is important because, for example, catabolic patients lose potassium in urine when nitrogen is lost from muscle. Likewise, anabolic patients retain more potassium as more nitrogen is incorporated into muscle tissue during recovery. Sodium and potassium in the nutritional product of the present invention are supplied by the SPH, sodium citrate, sodium chloride and potassium hydroxide. One hundred percent of the chloride requirement is provided by the SPH. The nitrogen/potassium ratio of the nutritional product of the present invention is about 3.5:1, which is believed will provide for some repletion of potassium lost with HIV related conditions such as vomiting and diarrhea. The electrolyte content of the nutritional product varies between flavors, but is generally in the following ranges: sodium, about 970 to 1050 mg per liter (230 to 249 mg per 8 fluid oz); potassium, about 2600 to 2830 mg per liter (620 to 670 mg per 8 fluid oz); and chloride, about 1400 to 1550 mg per liter (340 to 370 m9 per 8 fluid oz).

The major determinants of the osmolality of a nutritional product are simple carbohydrates, electrolytes, and amino acids or small peptides. Because the nutritional product of the present invention is formulated with a specific soy protein hydrolysate providing a high content of peptides and with elevated potassium levels to provide metabolic and physiologic advantages to the HIV infected patient, its osmolality is higher than isotonic. The osmolality of the nutritional product of the present invention is about 660 mosm/kg water.

The nutritional product of the present invention has a viscosity of about 24-45 cps and has been formulated for use both as an oral supplement and for total enteral support, either orally or by tube feeding. The density of the nutritional product at 23° C. is about 1.105 g/ml, and the pH of the nutritional product is about 6.4 to 6.6.

Two flavor systems have been developed for the new nutritional product: chocolate and orange cream. For the chocolate product, the amount of caffeine provided by the cocoa powder is approximately 8.38 mg per 8 fl. oz. or 41.9 mg per nutrient base. The level of theobromine is 52.4 mg per 8 fl. oz. or 262 mg per 1184 mL.

The process of manufacturing a nutritional formula for HIV/AIDS patients according to the present invention begins with the preparation of an oil blend containing the oils, emulsifier and oil soluble vitamins. Two more slurries (carbohydrate slurry and protein/mineral slurry) are prepared and mixed together with the oil blend to which a portion of the protein has been added. The resulting mixture is homogenized, heat processed, standardized with vitamins and minerals, flavored, and terminally sterilized. TABLES 7 and 8 are the bills of materials used in the manufacture of 1,000 kg batches of orange cream and chocolate products, respectively, according to the present invention.

TABLE 7

BILL OF MATERIALS FOR ORANGE CREAM FLAVOR PRODUCT

| COMPONENT | AMOUNT PER 1,000 kg (in kg) |
|---|---|
| Canola Oil | 15.10 |
| MCT Oil (fractionated coconut oil) | 4.31 |
| Diacetyl Tartaric Acid Esters of Mono and Diglycerides (Panodan ®) | 1.11 |
| Oil Soluble Vitamins Premix | 0.0585 |
| Alpha-tocopheryl Acetate | 0.04299 |
| Vitamin A Palmitate | 0.003574 |
| Phylloquinone | 0.000079 |
| Vitamin D3 | 0.0000097 |
| Coconut Oil (carrier) | Q.S. |
| Beta Carotene | 0.0188 |
| Sodium Caseinate | 13.34 |
| Water | 701.63 |
| Sucrose | 43.12 |
| Corn Syrup Solids | 136.18 |
| Sodium Citrate | 1.47 |
| Magnesium Phosphate dibasic | 0.7469 |
| Tricalcium Phosphate (preferably ultramicronized) | 0.0893 |
| Calcium Carbonate | 1.62 |

TABLE 7-continued

BILL OF MATERIALS FOR ORANGE CREAM FLAVOR PRODUCT

| COMPONENT | AMOUNT PER 1,000 kg (in kg) |
|---|---|
| Soy protein Hydrolysate | 52.87 |
| 45% KOH (proc. Aid) | 6.19 |
| Soy Polysaccharides | 10.43 |
| Iota Carrageenan | 0.3 |
| Kappa Carrageenan | 0.05 |
| Fish Oil high omega 3 | 2.16 |
| Ferrous Sulfate | 0.03476 |
| Manganous Sulfate | 0.0062 |
| Copper Sulfate | 0.0098 |
| Sodium Selenate | 0.00014 |
| Zinc Sulfate | 0.07035 |
| Water Soluble Vitamin Premix | 0.0875 |
| Niacinamide | 0.03286 |
| d-Calcium Pantothenate | 0.02126 |
| Pyridoxine Hydrochloride | 0.00522 |
| Thiamine Hydrochloride | 0.00543 |
| Riboflavin | 0.00424 |
| Folic Acid | 0.00074 |
| Biotin | 0.00064 |
| Cyanocobalamin | 0.000014 |
| Dextrose (carrier) | Q.S. |
| Taurine | 0.210 |
| L-Carnitine | 0.1460 |
| Potassium Iodide | 0.000158 |
| Choline Chloride | 0.2660 |
| Cyanocobalamin | 0.00007 |
| Ascorbic Acid | 0.7240 |
| Orange Cream Flavor | 4.00 |
| Artificial Fresh Cream | 3.5 |

TABLE 8

BILL OF MATERIALS FOR FORMULA CHOCOLATE FLAVOR PRODUCT

| COMPONENT | AMOUNT PER 1,000 kg (in kg) |
|---|---|
| Canola Oil | 14.5 |
| MCT Oil | 4.14 |
| Diacetyl Tartaric Acid Esters of Mono and Diglycerides (Panodan ®) | 1.07 |
| Oil Soluble Vitamins Premix | 0.0585 |
| Alpha-tocopheryl Acetate | 0.04299 |
| Vitamin A Palmitate | 0.003574 |
| Phylloquinone | 0.000079 |
| Vitamin D3 | 0.0000097 |
| Coconut Oil (carrier) | Q.S. |
| β- Carotene | 0.0188 |
| Sodium Caseinate | 13.34 |
| Water | 703.72 |
| Sucrose | 42.27 |
| Corn Syrup Solids | 133.49 |
| Sodium Citrate | 1.47 |
| Magnesium Phosphate dibasic | 0.461 |
| Tricalcium Phosphate (preferably ultramicronized) | 0.060 |
| Calcium Carbonate | 1.61 |
| Soy protein Hydrolysate | 54.87 |
| 45% KOH (proc. Aid) | 5.17 |
| Soy Polysaccharides | 9.92 |
| Iota Carrageenan | 0.3 |
| Kappa Carrageenan | 0.05 |
| Cocoa Powder | 8.0 |
| Fish Oil high omega 3 | 2.07 |
| Ferrous Sulfate | 0.03476 |
| Manganous Sulfate | 0.0062 |
| Copper Sulfate | 0.0098 |
| Sodium Selenate | 0.00014 |
| Zinc Sulfate | 0.07035 |
| Water Soluble Vitamin Premix | 0.0875 |
| Niacinamide | 0.03286 |
| d-Calcium Pantothenate | 0.02126 |
| Pyridoxine Hydrochloride | 0.00522 |
| Thiamine Hydrochloride | 0.00543 |
| Riboflavin | 0.00424 |

TABLE 8-continued

BILL OF MATERIALS FOR FORMULA CHOCOLATE FLAVOR PRODUCT

| COMPONENT | AMOUNT PER 1,000 kg (in kg) |
|---|---|
| Folic Acid | 0.00074 |
| Biotin | 0.00064 |
| Cyanocobalamin | 0.000014 |
| Dextrose (carrier) | Q.S. |
| Taurine | 0.1946 |
| L-Carnitine | 0.146 |
| Potassium Iodide | 0.000158 |
| Choline Chloride | 0.266 |
| Cyanocobalamin | 0.00007 |
| Ascorbic Acid | 0.724 |
| Artificial Chocolate Flavor | 1.4 |
| Artificial Fresh Cream | 3.5 |

An oil blend is prepared by adding the required amount of canola oil and MCT oil to a blend tank and heating the oils to a temperature of about 57°–68° C. (135°–155°F.) with agitation. The required quantity of the Panodan ® emulsifier, (diacetyl tartaric acid esters of mono and diglycerides), is added to the heated oil blend. The oil soluble vitamins premix and beta carotene are then added and mixed well to insure proper blending.

A protein-in-fat slurry is prepared by adding to the oil blend one half of the sodium caseinate while agitation is maintained. This slurry is kept at a temperature of about 40°–46° C. (105°–115° F.) until use.

A carbohydrate slurry is prepared by weighing the appropriate amount of water in a suitable tank and heating the water to a temperature of about 68°–74° C. (155°–165° F.). Sucrose and corn syrup solids are added under agitation to make a 60% solution, by weight.

A mineral/protein slurry is prepared by weighing the appropriate amount of water and heating the water to a temperature of about 68°–74° C. (155°–165° F.). The following ingredients are dissolved/suspended in the water with agitation in the following order: sodium citrate, magnesium phosphate dibasic, tricalcium phosphate, calcium carbonate, soy protein hydrolysate and mixed well until it is completely dissolved, to yield a 27% slurry by weight. The pH of the mineral/protein slurry is then adjusted to about 5.7–6.0 with 45% KOH.

A blend is prepared by heating the appropriate amount of water to a temperature of about 57°–68° C. (135°–150° F.) and adding the remaining sodium caseinate, soy polysaccharides, iota carrageenan and kappa carrageenan. For chocolate flavored batches, the needed amount of cocoa powder is then added and mixed well to insure homogeneity. A mixing apparatus such as the two stage blender which is described in U.S. Pat. No. 4,850,704, which is incorporated herein for the purpose of teaching appropriate equipment for practicing the invention, may be used in making this blend.

The carbohydrate slurry, the mineral/protein slurry and the protein-in-fat slurry are combined together with agitation to yield a blend having 34% solids, by weight. The pH of the blend should be in the range of 6.25–6.55. If an adjustment of pH is needed, 1N KOH or 1N citric acid are added. Prior to emulsification fish oil is metered into the blend at a constant rate such that the dispersion of fish oil is uniform throughout the blend.

The blend is emulsified, ultra-high temperature processed (299°–304° F.), then homogenized at 3900–4100/500±100 psig using 2 stage homogenizer. The processed blend is then cooled to 1°–7° C. (34°–45° F.).

A solution of vitamins, amino acids and minerals containing about 9.0% solids by weight, is prepared by heating the appropriate amount of defluoridized water to a temperature of about 43°–54° C. (110°–130° F.). The minerals are then added with agitation, preferably in the following order: ferrous sulfate, manganous sulfate, copper sulfate, sodium selenate and zinc sulfate and potassium iodide. The vitamins and amino acids are added with agitation in the following order: water soluble vitamin premix, taurine, L-carnitine, choline chloride, and cyanocobalamin. The solution of vitamins and minerals is then added to the blend, with agitation.

An ascorbic acid solution, 12% solids, is prepared by combining the required amount of 45% KOH with cold ingredient water and adding the required amount of ascorbic acid. Once the pH is determined to be in the range of 6–10, the ascorbic acid solution is added, with agitation, to the blend.

For the orange cream flavor, the flavor solution is prepared by combining the necessary amount of water, at a temperature of about 38°–49° C. (100°–120° F.), with the orange cream flavor. The artificial fresh cream is then added. For the chocolate flavor product, the flavor solution is prepared by mixing the necessary amount of water, at a temperature of about 38°–49° C. (100°–120° F.), the artificial chocolate flavor, and the artificial fresh cream. In each instance the flavor solution contains about 20% solids. The flavor solution is added, with agitation, to the blend.

The pH of the complete blend is adjusted to 6.6–6.8 with 1N KOH or 1N citric acid, placed in suitable container, such as 8 oz. metal cans, and terminally sterilized. Of course, if desired, the nutritional product may be manufactured using aseptic methods, and packaged in suitable containers.

The nutritional product manufactured by the method described herein is a ready-to-serve liquid which can be consumed orally or be tube-fed. While the nutritional product of the present invention has only been manufactured in a ready-to-feed liquid form, it is understood that it may be produced in a concentrated liquid form for later dilution or in powder form for later reconstitution with a suitable liquid without deviating from the scope of the present invention.

A study has been conducted with the enteral nutritional product of the present invention. This study was designed to assess the relative effects of the nutritional product of the present invention as compared to a standard enteral whole protein-based formula, Ensure ® on numerous prognostic markers of nutritional, immune, and gastrointestinal status and function in HIV infected and AIDS patients. Ensure ® is distributed commercially by Ross Laboratories, a Division of Abbott Laboratories, Columbus, Ohio, U.S.A. A comparison of these two products is presented in TABLE 9.

Upon entrance into the study, patients were randomly assigned to either the group fed the product of the present invention (n=17) or the control (Ensure ®) group (n=22), and instructed to consume at least 16 oz. of the respective enteral nutritional product per day as supplement to their normal routine intake for an initial period lasting 6 weeks. Total dietary intake (supplement plus other food consumed) was monitored throughout the study using serial 7-day food intake records and revealed no significant differences in overall intake of protein, fat or carbohydrate between the two groups.

Baseline assessment of age, height, weight, and weight loss also revealed no significant differences between the two groups. Baseline and follow-up (at 6 weeks) blood samples were obtained in the fasting state and used for the measurement of biochemical indicators of nutritional and immune status. In addition, detailed assessment of body compositional changes (anthropometrics and bioelectrical impedance) and of clinical outcome variables including, but not limited to, bowel habits, Karnofsky performance score, hospitalizations, medication usage, and cardiac performance, were obtained at both baseline and at the six week follow-up. In order to assess gastrointestinal integrity and function, as well as the relative enterotrophic effects of the respective enteral supplements on these parameters, duodenal biopsies were obtained at both baseline and at follow-up in a subset population (new product, n=6; Ensure®, n=5) from this study, and biopsy samples were evaluated for histological and morphometric parameters via transmission electron microscopy.

From the population of HIV infected and AIDS patients being followed at a major medical center, 39 patients with HIV infection including patients diagnosed with ARC and AIDS were studied over a 6 week period. Subjects ranged from 13 to 60 years of age. Subjects were entered into the study without regard to sex or race. Patient eligibility criteria included individuals with confirmed HIV infection, a favorable Karnofsky performance status (65-100) and adequate hematologic (WBC greater than 200/mm2, platelets greater than 100,000), renal (serum creatinine less than 2 mg/dl) and hepatic (bilirubin less than 2 mg/dl) functions. In addition, patients who had lost more than 30% of their ideal body weight were excluded from entry into the study. All data and samples from individuals participating in this study were collected respectively in conjunction with nutrition data collection visits. This was a double-blinded prospective study.

The results indicated that the enteral nutritional product disclosed herein significantly supports immune function, GI symptomology, physical performance, and positive trends in body composition when contrasted with a standard enteral feeding (Ensure®) over the treatment period. These results provide significant data for support of the efficacy of the product disclosed herein in the HIV/AIDS patient.

TABLE 9

NUTRIENT PROFILES OF CONTROL (ENSURE ®) NUTRITIONAL PRODUCT OF THE PRESENT INVENTION (ANALYSIS OF PRODUCTS USED IN STUDY)

| NUTRIENT (per 8 fl. oz) | ENSURE ® | NEW PRODUCT |
|---|---|---|
| Energy, kcal. | 250 | 303 |
| Protein, g | 8.8 | 14.2 |
| Carbohydrate, g | 34.3 | 51.1 |
| Fat, g | 8.8 | 5.4 |
| B-carotene, (mg) | — | 1.2 |
| Vitamin A, IU | 625 | 1000 |
| Vitamin D, IU | 50 | 80 |
| Vitamin E, IU | 5.6 | 9.0 |
| Vitamin K, mcg | 9 | 16 |
| Vitamin C, mg | 37.5 | 90.0 |
| Folic acid, mcg | 100 | 120 |
| Thiamine, mg | 0.38 | 0.75 |
| Riboflavin, mg | 0.43 | 0.68 |
| Vitamin B-6, mg | 0.5 | 0.8 |
| Vitamin B-12, mcg | 1.5 | 12.0 |
| Niacin, mg | 5.0 | 6.0 |
| Choline, mg | 75 | 50 |
| Biotin, mcg | 75 | 90 |
| Pantothenic acid, mg | 2.5 | 3.0 |

TABLE 9-continued

NUTRIENT PROFILES OF CONTROL (ENSURE ®) NUTRITIONAL PRODUCT OF THE PRESENT INVENTION (ANALYSIS OF PRODUCTS USED IN STUDY)

| NUTRIENT (per 8 fl. oz) | ENSURE ® | NEW PRODUCT |
|---|---|---|
| Sodium, mg | 200 | 240 |
| Potassium, mg | 370 | 620 |
| Chloride, mg | 310 | 350 |
| Calcium, mg | 125 | 200 |
| Phosphorus, mg | 125 | 200 |
| Magnesium mg | 50 | 80 |
| Iodine, mcg | 18.8 | 30.0 |
| Manganese, mg | 0.62 | 1.25 |
| Copper, mg | 0.25 | 0.60 |
| Zinc, mg | 2.82 | 3.75 |
| Iron, mg | 2.25 | 4.50 |
| Selenium, mcg | — | 14 |
| Chromium, mcg | — | 20 |
| Molybdenum, mcg | — | 30 |
| L-carnitine, mg | — | 30 |
| Taurine, mg | — | 50 |

TABLE 10 presents a concise summary of the more significant changes which were observed in this six week supplement protocol. The arrows and their respective statistical significance are indicated for the comparison of follow-up to baseline (change from baseline) for both the control and new product groups. An overall review of the variables indicated in TABLE 10 reveal that many, if not most of the parameters, either are significantly different or are approaching statistical significance in the control group, while most of the parameters in the new product group are maintained or do not change.

TABLE 10

SUMMARY OF CLINICALLY SIGNIFICANT RESULTS

| PARAMETER | (WEEK 0 vs 6) CONTROL | (WEEK 0 vs 6) NEW PRODUCT |
|---|---|---|
| WBC ($\times 10^3$ cells/mm$^3$) | ↑ NS ($p = 0.2136$) | – NS ($p = 0.8409$) |
| LYMPHOCYTES (%) | ↓ ($P = 0.0003$) | – NS ($P = 0.8502$) |
| NEUTROPHILS (%) | ↑ ($P = 0.0055$) | – NS ($p = 0.7255$) |
| IGA (mg/dL) | ↑ ($p = 0.0370$) | ↑ ($p = 0.0309$) |
| TOTAL LYMPHOCYTES ($\times 10^3$ cells/mm$^3$) | ↓ TREND ($p = 0.0581$) | – NS ($p = 0.9570$) |
| CD4 (cells/mm$^3$) | ↓ TREND ($p = 0.0663$) | – NS ($p = 0.3373$) |
| CD8 (cells/mm$^3$) | ↓ TREND ($p = 0.0756$) | ↑ NS ($p = 0.9341$) |
| CD4/CD8 Ratio | ↓ NS ($p = 0.7096$) | ↓ NS ($p = 0.8512$) |
| CD4/Albumin Ratio | ↓ ($p = 0.0483$) | ↓ NS ($p = 0.4887$) |
| BOWEL HABITS (AVG #) | ↓ TREND ($p = 0.1060$) | ↓ TREND ($p = 0.0869$) |
| KARNOFSKY SCORE | ↓ NS ($p = 0.5781$) | – NS ($p = 1.000$) |
| BUN (mg/dL) | ↑ ($p = 0.0324$) | – NS ($p = 0.4836$) |
| CREATININE (mg/dL) | – NS ($p = 0.3489$) | ↑ TREND ($p = 0.0781$) |

Note:
(a) In this Table if "p" is greater than 0.05 the result is not significant; if "p" is equal to or less than 0.05 the result is highly significant; and if "p" is equal to or less than 0.12 the result shows a strong trend.
(b) In this table "NS" means not significant.

Total lymphocytes in the group fed the nutritional product of the present invention increased, while they fell in the control group. CD8 lymphocytes increased in the group fed the nutritional product of the present invention (NS), and again fell in the control group. Conversely, CD4 cell counts showed a strong trend in the control group, but were unchanged in the new product group. In contrast, CD4:CD8 ratios which decrease with AIDS progression, decreased to a greater extent in the control group as compared to the new product group. In addition to enhanced or maintained function in the new product group, this group experienced a reduction in GI symptomology, significant trends in body composition maintenance, maintenance of physical performance, improved cardiac function as measured by increased respiratory sinus arrhythmia amplitude, and significant GI tolerance (the latter contrary, but the specific efficacy of the nutritional product of the present invention is where such efficacy may possibly be linked to reduced immune cell death (apoptosis).

White blood cell count (WBC) was increased in the control group while no change was apparent in the new product group. Although not statistically different, WBC increased from $3.2 \pm 0.3$ to $4.4 \pm 0.7$ cells $\times 10^3/\text{mm}^3$ in the control group. This increase in WBC in the control group was apparently due to a significantly elevated neutrophil count in the control group after six weeks of supplement use. In addition to the elevation in neutrophil count, the percent of white blood cells due to lymphocytes was reduced in the control group after six weeks of the supplement use. There was no change in percent lymphocytes between baseline and follow-up in the new product group. These changes in WBC and certain of its respective components indirectly suggest that the control group was more immunocompromised than the new product group at follow-up (after six weeks of supplement use).

None of the parameters presented demonstrated any significant difference between the two groups at baseline, indicating the similar immune status of all patients upon entry into the study. However, as discussed above in the assessment of white blood cell count and its respective constituents, total lymphocyte count was significantly decreased in the control group after six weeks of the supplementation. Although not statistically significant, the mean absolute number of total lymphocytes decreased in the control group while it increased in the new product group after six weeks of supplementation. In addition, both CD4 and CD8 levels, excellent prognostic markers of AIDS progression, decreased in the control group after six weeks of supplementation. Conversely, CD4 levels in the new product group were maintained at baseline levels and CD8 levels actually increased after six weeks of supplementation. There appears to be a definitive trend in these markers of AIDS progression suggesting that the patients fed the new product were better able to maintain immunocompetence throughout the course of the study as compared to the controls. Further evidence of this maintained immune status is presented in TABLE 10. Both CD4/CD8 and CD4/albumin ratios decreased to a much greater degree in the control group (23% and 15%, respectively as compared to the new product group (4% and 6%, respectively). Once again, although not statistically significant in all cases, these results are clearly indicative of a trend and further confirm the observation that the patients fed the new product were better able to maintain their immune status as compared to the controls. Additional support for this contention comes from the results presented in TABLE 11. This table presents an assessment of the number of patients in both groups that progressed to CD4 levels below 150 after six weeks of supplementation. The results clearly demonstrate that supplementation with the new product is able to prevent the fall of CD4 to a level below 150 in a larger proportion of patients than the control supplement.

TABLE 11

|  | CONTROL GROUP | NEW PRODUCT GROUP |
| --- | --- | --- |
| CD4% Change 1.5 mo. | −19% | NC (No Change) |
| CD4% Change 1.5 mos. Patient with CD4 > 150 | −43% | +14% |
| CD4% Change 1.5 mos. Patients with CD4 < 150 | +23% | −20% |

Apoptosis, also referred to as programmed cell death, is an active cell suicide process that depends on the environment, in particular on the nature and intensity of activation signals received by cells. Apoptosis involves chromatic condensation, membrane blebbing and fragmentation of DNA, all of which are clearly visible upon microscopic examination. On the other hand, cell death due to necrosis, caused, for example, by trauma or disease, has results which are clearly distinguishable from apoptotic cells upon microscopic examination. Apoptosis of CD4 cells in both HIV positive and AIDS patients has been reported in reputable scientific publications, for example: Gougeon, "Apoptosis as a Mechanism of Cell Death in Peripheral Lymphocytes from HIV-1-Infected Individuals", IMMUNODEFICIENCY IN HIV INFECTION AND AIDS, pages 115-126 (1992); and Ameisen, "THE PROGRAMMED CELL DEATH THEORY OF AIDS PATHOGENESIS: IMPLICATIONS, TESTABLE PREDICTIONS, AND CONFRONTATION WITH EXPERIMENTAL FINDINGS", IMMUNODEFICIENCY REVIEWS, Vol. 3, pages 237-246 (1992). Since priming for apoptosis has been reported to occur early in the course of the disease, any possible intervention should be initiated early in order to be most effective. While at the present time the effect an intervention in the apoptosis of CD4 cells in HIV positive and AIDS patients may have on the further course of the disease, it has known that the depletion of CD4 cells leads to loss of immune functions which eventually results in the patient being subjected to opportunistic infections. The data presented in TABLES 10 and 11, and the accompanying remarks, clearly indicated that enteral nutritional support of a person infected with human immunodeficiency virus with the nutritional product disclosed herein impedes the apoptosis of CD4 cells. That is to say this nutritional support does not absolutely eliminate apoptosis of CD4 cells, but it appears that some component of the nutritional product interferes with the transmission of signals to CD4 cells which initiate apoptosis. It is believed that the soy protein hydrolysate used in the nutritional product provides some agent, perhaps a peptide, which results in this beneficial biological effect. Enterally providing this soy protein hydrolysate in a therapeutically effective quantity is believed to impede the apoptosis of CD4 cells in a person infected with immunodeficiency virus.

In addition to the above assessments of immune status, immunoglobulin levels for IgG, IgM, and IgA were also assessed at both baseline and after six weeks of supplementation at follow-up. No statistical differences were observed for each of these parameters at baseline when control and new product supplemented patients were compared. However, after six weeks of supplementation, each immunoglobulin level had increased. IgG, although increased in both groups, were not significantly increased in either group. However, the increase in IgG in the control group resulted in a mean value which was outside of the clinically normal range, while the increased mean value in the group fed the new product remained within normal clinical ranges. As was the case of IgG, IgM mean levels were also increased in both groups (statistically elevated in the group fed the new product). However, mean IgM levels in both groups remained within the normal clinical range. IgA were statistically elevated in both the control and the group fed the new product after six weeks.

TABLE 10 presents the change in the average number of bowel movements per day for the control and new product groups. Interestingly, enteral supplement appeared to decrease the mean number of bowel movements per day in both supplement groups. Although not statistically significant, the average number of bowel movements per day decreased by almost 1 per day in both groups after six weeks of supplementation. When the data from both groups were pooled together the average number of bowel movements per day were significantly decreased at follow-up from baseline. This is an interesting finding since enteral supplementation has not commonly been shown to result in a decrease in average number of bowel movements per day, but rather has been reported to be associated with an increase in this parameter. In addition to subjectively recording the average number of bowel movements per day, patients also provided detailed information with regard to stool consistency. There were no significant differences between the two study groups with regard to stool consistency either at baseline or after six weeks of supplementation. Furthermore, the respective nutritional supplements appeared to have no effect on the change from baseline with regard to stool consistency.

Another important clinical outcome variable measured in this study was the Karnofsky score. The Karnofsky score provides a subjective assessment of quality of life made by a patient's personal physician. TABLE 10 presents the change in the Karnofsky scores for the control and new product supplemented groups. At baseline, both study groups were nearly identical with regard to functional status (76 vs. 80 for the control and new product group respectively). However, although not statistically different, it is clear that the average Karnofsky scores in the control group declined to a larger degree (21%) than those of the new product group (9%) over the course of the six week study.

The only biochemistries which demonstrated clinically significant changes were creatinine and blood urea nitrogen (BUN). Serum creatinine, although not statistically significant, increased from $1.0 \pm 0.1$ to $1.1 \pm 0.1$ mg/dL in the new product group after six weeks of supplement use while no change was observed in the control group. Conversely, BUN significantly increased from 14 to 15 mg/dL in both the control and new product groups. This increase in BUN was only statistically significant in the control group. Together, these observations suggest that the patients receiving the control supplement had a larger degree of protein breakdown as compared to the new product group and that the new product group was better able to increase muscle mass during the course of the study than the controls (as indirectly evidence by an increased creatinine level after six weeks of supplementation).

In an attempt to assess the enterotrophic effects of the new product and its constituent soy protein hydrolysate (SPH), fish oils, and soluble fiber system, terminal duodenal biopsies were obtained in a subset population of patients enrolled in this study. Six control patients and 7 patients fed the new product had baseline and six week follow-up biopsies obtained via direct endoscopy. Biopsy samples were fixed in glutaraldehyde and processed for electron microscopic analysis. No significant differences either between groups at baseline and follow-up or between change from baseline for the respective supplement groups were observed for microvillus height, microvillus diameter and microvillus surface area.

Standard anthropometric variables and their respective calculated body composition parameters were recorded. The data clearly demonstrate no significant differences or changes between any of these parameters for both study groups. It should be noted, however, that although no significant improvements were observed, both supplements were able to maintain individual anthropometric variables as well as body compartments including fat mass, fat-free mass, and percent body fat. Based on the fact that the patients enrolled in this study were reporting significant weight loss (10% from usual) upon entry into the study, this alone provides clear evidence that enteral supplementation can reduce or prevent the progressive weight loss associated with the progression of AIDS.

Another very important and costly consequence of HIV-infection and/or AIDS is the requirement of multiple hospitalizations. Five of the 22 control group patients (23%) required at least one additional hospitalization during the course of this six week study while none of the new product supplemented patients required an additional hospitalization ($p < 0.05$). The cost of a single hospitalization for treatment of AIDS related complications is enormous. This finding therefore warrants further investigation.

I claim:

1. A method of impeding the apoptosis of CD4 cells in a person infected with human immunodeficiency virus comprising enterally feeding to said person a therapeutically effective amount of an enteral nutritional product comprising:
    (a) a soy protein hydrolysate having a degree of hydrolysis in the range of about 14 to 17 and a molecular weight partition, as determined by size exclusion chromatography wherein 30%-60% of the particles have a molecular weight in the range of 1500-5000 Daltons and the amino acid profile of the soy protein hydrolysate has less than 1% free amino acids;
    (b) a second source of protein which comprises a source of intact protein in a quantity sufficient to yield a stable emulsification of the soy protein hydrolysate and the intact protein in the nutritional product; and
    (c) a source of fat characterized by the ratio, by weight, of the sum of the n-6 fatty acids to the sum of the n-3 fatty acids being in the range of about 1.3:1 to 2.5:1.

2. A method of impeding the apoptosis of CD4 cells in a person infected with human immunodeficiency virus as described in claim 1 wherein the soy protein hydrolysate has the following amino acid profile in g/100 g of the soy protein hydrolysate:

| | | |
|---|---|---|
| Aspartic acid | 9.8–10.4 |
| Threonine | 2.9–3.2 |
| Serine | 3.7–4.4 |
| Glutamic Acid | 17.0–18.1 |
| Proline | 4.4–4.9 |
| Glycine | 3.2–3.3 |
| Alanine | 3.0–3.2 |
| Valine | 2.9–3.6 |
| Methionine | 0.9–1.1 |
| Isoleucine | 3.0–3.7 |
| Leucine | 5.1–5.3 |
| Tyrosine | 2.7–2.9 |
| Phenylalanine | 3.3–3.5 |
| Histidine | 2.0–2.2 |
| Lysine | 5.5–5.8 |
| Arginine | 6.3–6.7 |
| Tryptophan | 0.3–0.7 |
| Cystine | 1.3–1.4 |

3. A method of impeding the apoptosis of CD4 cells in a person infected with human immunodeficiency virus as described in claim 1 wherein the soy protein hydrolysate has the following mineral profile:

| | |
|---|---|
| Calcium, mg/100 g | 170–350 |
| Sodium, mg/100 g | 370–650 |
| Potassium, mg/100 g | 180–600 |
| Magnesium, mg/100 g | 270–550 |
| Phosphorus, mg/100 g | 900–1500 |
| Chloride, mg/100 g | 1400–2500 |
| Iron, mg/100 g | 13–25 |
| Zinc, mg/100 g | 3–6 |
| Manganese, mg/100 g | 4–8 |
| Copper, mg/100 g | 0.5–1.5 |
| Vanadium, ppm | trace–15 |
| Selenium, ppb | trace–350 |
| Chromium, ppm | trace–2.9 |
| Molybdenum, ppm | trace–3.7 |

4. A method of impeding the apoptosis of CD4 cells in a person infected with human immunodeficiency virus as described in claim 2 wherein the soy protein hydrolysate has the following mineral profile:

| | |
|---|---|
| Calcium, mg/100 g | 170–350 |
| Sodium, mg/100 g | 370–650 |
| Potassium, mg/100 g | 180–600 |
| Magnesium, mg/100 g | 270–550 |
| Phosphorus, mg/100 g | 900-1500 |
| Chloride, mg/100 g | 1400–2500 |
| Iron, mg/100 g | 13–25 |
| Zinc, mg/100 g | 3–6 |
| Manganese, mg/100 g | 4–8 |
| Copper, mg/100 g | 0.5–1.5 |
| Vanadium, ppm | trace–15 |
| Selenium, ppb | trace–350 |
| Chromium, ppm | trace–2.9 |
| Molybdenum, ppm | trace–3.7 |

5. A method of impeding the apoptosis of CD4 cells in a person infected with human immunodeficiency virus as described in claim 1 wherein the soy protein hydrolysate is further characterized in that a 5% slurry, by weight, has a pH of less than 4.5.

6. A method of impeding the apoptosis of CD4 cells in a person infected with human immunodeficiency virus as described in claim 1 wherein the soy protein hydrolysate comprises, by weight,:
   (a) not less than 80% protein;
   (b) not more than % fat; and
   ( c ) not more than 5.5% ash.

7. A method of impeding the apoptosis of CD4 cells in a person infected with human immunodeficiency virus as described in claim 1 wherein the soy protein hydrolysate was hydrolyzed with an alkaline proteinase.

8. A method of impeding the apoptosis of CD4 cells in a person infected with human immunodeficiency virus as described in claim 1 wherein the degree of hydrolysis is about 16.0.

9. A method of impeding the apoptosis of CD4 cells in a person infected with human immunodeficiency virus as described in claim 2 wherein the degree of hydrolysis is about 16.0.

10. A method of impeding the apoptosis of CD4 cells in a person infected with human immunodeficiency virus as described in claim 3 wherein the degree of hydrolysis is about 16.0.

11. A method of impeding the apoptosis of CD4 cells in a person infected with human immunodeficiency virus as described in claim 4 wherein the degree of hydrolysis is about 16.0.

12. A method of impeding the apoptosis of CD4 cells in a person infected with human immunodeficiency virus as described in claim 5 wherein the degree of hydrolysis is about 16.0.

13. A method of impeding the apoptosis of CD4 cells in a person infected with human immunodeficiency virus as described in claim 6 wherein the degree of hydrolysis is about 16.0.

14. A method of impeding the apoptosis of CD4 cells in a person infected with human immunodeficiency virus as described in claim 7 wherein the degree of hydrolysis is about 16.0.

15. A method of impeding the apoptosis of CD4 cells in a persons infected with human immunodeficiency virus as described in claim 1 wherein the enteral nutritional product further comprises a source of dietary fiber.

16. A method of impeding the apoptosis of CD4 cells in a person infected with human immunodeficiency virus as described in claim 1 wherein the enteral nutritional product further comprises soy polysaccharide as a source of dietary fiber.

* * * * *

UNITED STATES PATENT AND TRADEMARK OFFICE
CERTIFICATE OF CORRECTION

PATENT NO. : 5,330,972
DATED : July 19, 1994
INVENTOR(S) : F. O. Cope It is certified that error appears in the above-identified patent and that said Letters Patent is hereby corrected as shown below:

Column 6, line 43 change "Artson" to --Anson--

Column 9, table 5 change "Iryptophan" to --Tryptophan--

Signed and Sealed this

Twenty-seventh Day of September, 1994

Attest:

BRUCE LEHMAN

*Attesting Officer*  *Commissioner of Patents and Trademarks*